(12) United States Patent
Desos et al.

(10) Patent No.: US 7,494,994 B2
(45) Date of Patent: Feb. 24, 2009

(54) PHENYLPYRIDYLPIPERAZINE COMPOUNDS

(75) Inventors: Patrice Desos, Bios-Colombes (FR); Alexis Cordi, Suresnes (FR); Pierre Lestage, La Celle-Saint-Cloud (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 209 days.

(21) Appl. No.: 11/432,250

(22) Filed: May 11, 2006

(65) Prior Publication Data

US 2006/0258670 A1 Nov. 16, 2006

(30) Foreign Application Priority Data

May 12, 2005 (FR) .................................. 05 04758

(51) Int. Cl.
- A61K 31/4418 (2006.01)
- C07D 213/72 (2006.01)
- C07D 213/74 (2006.01)

(52) U.S. Cl. ................ 514/235.8; 514/253.01; 514/253.09; 514/253.13; 544/121; 544/360; 544/364

(58) Field of Classification Search ........................ None
See application file for complete search history.

(56) References Cited

U.S. PATENT DOCUMENTS

2003/0236259 A1* 12/2003 Hohlweg et al. ............ 514/242

FOREIGN PATENT DOCUMENTS

| EP | 0361489 | 4/1990 |
|----|---------|--------|
| WO | 92/05156 | 4/1992 |
| WO | 99/21834 | 5/1999 |

OTHER PUBLICATIONS

Phillips et al. Annual Reports in medicinal Chemistry, vol. 33, pp. 31-40 (1998).*
Passani et al. Neuroscience and Biobehavioral Reviews, vol. 24, p. 107-113 (2000).*
Leurs et al. TIPS, vol. 19, p. 177-183 (1998).*
Hohlweg et al. Chemical Abstracts, vol. 146, No. 142682 (2007) Abstract for WO 2007/003604 (Jan. 11, 2007).*
Philippu, et al., *Behav. Brain Res.*, 2001, 124, 151-159.
Bacciottini, et al., *Behav. Brain Res.*, 2001, 124, 183-194.
Alvarez, et al., *Behav. Brain Res.*, 2001, 124, 195-202.
Kim, et al., *Neuroscience Letters*, 2002, 321, 169-172.
Leurs, et al., *TiPS*, 1998, vol. 19, 177-183.
Tozer, et al., *Exp. Opin. Ther. Patents*, 2000, 10, 1045-1055.
Passani, et al., *Neurosci. Biobehav. Rev.*, 2000, 24, 107-113.
Fox, et al., *J. Pharm. Exper. Ther.*, 2003, 305, 897-908.
Ligneau, et al., *J. Pharm. Exper. Ther.*, 1998, 287, 658-666.
Monti, et al., *Eur. J. Pharmacol.*, 1991, 205, 283-287.
Stark, et al., *Drugs of the Future*, 1996, 21, 507-520.
Howard, *Exp. Opin. Ther. Patents*, 2000, 10, 1549-1559.
Itoh, et al., *Biol. Psychiatry*, 1999, 45, 475-481.
Masaki, et al., *Diabetes*, 2001, 50, 376-384.
Masaki, et al., *Endocrinology*, 2003, 144, 2741-2748.
Rouleau, et al., *J. Pharm. Exper. Ther.*, 1997, 281, 1085-1094.

* cited by examiner

*Primary Examiner*—Emily Bernhardt
(74) *Attorney, Agent, or Firm*—Hueschen and Sage

(57) ABSTRACT

A compound selected from those of formula (I):

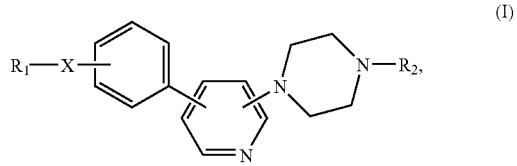

wherein:
X represents a C(O) or $SO_2$ group,
$R_1$ represents an aryl group or a group $NR_3R_4$ wherein $R_3$ and $R_4$ are as defined in the description,
$R_2$ represents an alkyl, $(C_3-C_8)$cycloalkyl or $(C_3-C_8)$cycloalkyl-$(C_1-C_6)$alkyl group,
its isomers, and addition salts thereof,
and medicinal products containing the same which are useful in treating conditions treatable by antagonists of type $H_3$ central histamine receptors.

10 Claims, No Drawings

PHENYLPYRIDYLPIPERAZINE COMPOUNDS

The present invention relates to new phenylpyridylpiperazine compounds, to a process for their preparation and to pharmaceutical compositions containing them.

The compounds of the present invention are especially valuable from a pharmacological point of view because of their specific interaction with type $H_3$ central histamine receptors and can be used in the treatment of neuropathoiogies associated with cerebral ageing, mood disorders, eating behaviour and sleep-wakefulness rhythm, and of attention deficit hyperactivity syndrome.

Ageing of the population due to increased life expectancy at birth has brought with it a large increase in the incidence of age-related neuropathologies and especially of Alzheimer's disease. The principal clinical manifestations of cerebral ageing and especially of age-related neuropathologies are deficiencies in memory and cognitive functions, which may lead to dementia.

Recent neuropharmacological studies have shown that, in the central nervous system, histamine, via the central histaminergic systems, has the role of a neurotransmitter or neuromodulator in physiological or physiopathological situations (Annu. Rev. Neurosci., 1986, 9, 209-254; Physiol. Rev., 1991, 71, 1-51). Thus, it has been shown that histamine is involved in various physiological and behavioural processes, such as thermoregulation, neuro-endocrinal regulation, circadian rhythm, cataleptic states, motility, aggressiveness, eating behaviour, learning and memorisation, and synaptic plasticity (Hass et al., histaminergic neurones: morphology and function, Boca Raton, Fla.: CRC Press, 1991, pp. 196-208; Prog. Neurobiology, 2001, 63, 637-672).

Of the 3 histamine receptor sub-types ($H_1$, $H_2$ and $H_3$), it was initially shown that the type $H_3$ receptor is a pre-synaptic autoreceptor which controls the release of histamine (Nature, 1987, 327, 117-123). Its activation inhibits the release and synthesis of histamine by a negative feedback mechanism (Neuroscience, 1987, 23, 149-157). The existence of presynaptic heteroreceptors capable of modulating the release of some neuropeptides and of many neurotransmitters, such as noradrenaline, serotonin, dopamine, GABA, acetylcholine and glutamate, was demonstrated subsequently (TiPS, 1998, 9 177-183). Studies carried out in animals have shown that an increase in endogenous extra-synaptic levels of histamine via blockage of type $H_3$ receptors by $H_3$ antagonists makes it possible to promote states of vigilance, learning and memory processes, to regulate food intake, and to combat convulsive attacks (Prog. Neurobiol., 2000, 63, 637-672; Neurosci. Biobehav. Rev., 2000, 24, 107-113). As a result, the potential therapeutic indications for $H_3$ antagonists are the treatment of cognitive deficiencies associated with cerebral ageing and with neurodegenerative diseases such as Alzheimer's disease, Parkinson's disease, Pick's disease, Korsakoff's disease and frontal or sub-cortical dementias of vascular or other origin, and the treatment of mood disorders, convulsive attacks, attention deficit hyperactivity syndrome, obesity, pain and narcoleptic states.

The compounds of the present invention, in addition to having a novel structure, have pharmacological properties which are entirely surprising and valuable in this field.

More specifically, the present invention relates to compounds of formula (I):

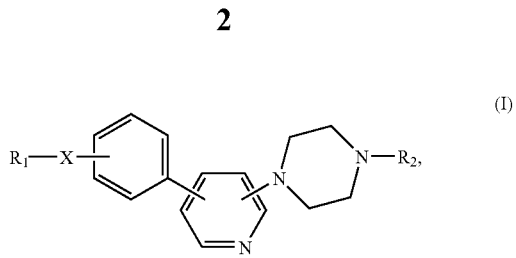

wherein:
X represents a C(O) or $SO_2$ group,
$R_1$ represents:
  an aryl group,
  or a group $NR_3R_4$ wherein $R_3$ and $R_4$, which may be the same or different, each represent a hydrogen atom or a linear or branched ($C_1$-$C_6$)alkyl group, a ($C_3$-$C_8$)-cycloalkyl group or a ($C_3$-$C_8$)cycloalkyl-($C_1$-$C_6$)alkyl group in which the alkyl moiety is linear or branched,
  or $R_3$ and $R_4$, together with the nitrogen atom carrying them, form a 5- to 8-membered ring wherein one of the carbon atoms may be replaced by a nitrogen, oxygen or sulphur atom or by an SO or $SO_2$ group, the ring thereby defined optionally being bridged by a linear or branched ($C_1$-$C_6$)alkyl group and/or optionally being substituted by one or more identical or different groups selected from halogen, linear or branched ($C_1$-$C_6$)alkyl, ($C_3$-$C_8$) cycloalkyl, linear or branched ($C_1$-$C_6$)alkoxy, linear or branched ($C_1$-$C_6$)polyhaloalkyl, carboxy, hydroxy, cyano, oxo, nitro and amino (optionally substituted by one or more linear or branched ($C_1$-$C_6$)alkyl groups),
$R_2$ represents a linear or branched ($C_1$-$C_6$)alkyl group, a ($C_3$-$C_8$)cycloalkyl group or a ($C_3$-$C_8$)cycloalkyl-($C_1$-$C_6$) alkyl group wherein the alkyl moiety may be linear or branched,
to their enantiomers and diastereoisomers, and also to addition salts thereof with a pharmaceutically acceptable acid or base, it being understood that:
an aryl group means the groups phenyl, naphthyl and biphenyl, those groups optionally being substituted by one or more identical or different groups selected from halogen, linear or branched ($C_1$-$C_6$)alkyl, linear or branched ($C_1$-$C_6$) alkoxy, linear or branched ($C_1$-$C_6$)polyhaloalkyl, carboxy, hydroxy, cyano, nitro and amino (optionally substituted by one or more linear or branched ($C_1$-$C_6$)alkyl groups).

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Preferred compounds according to the invention are compounds of formula (I) wherein $R_1$ represents an $NR_3R_4$ group.

The invention relates more especially to compounds of formula (I) wherein $R_3$ and $R_4$, together with the nitrogen atom carrying them, form a 5- to 8-membered ring wherein one of the carbon atoms may be replaced by a nitrogen, oxygen or sulphur atom or by an SO or $SO_2$ group, the ring thereby defined optionally being bridged by an alkyl chain and unsubstituted or substituted, preferably by one or more halogen atoms, for example fluorine, or by an alkyl group, for example a methyl group.

Even more preferably, preferred $R_1$ groups are the groups morpholinyl, thiomorpholinyl, piperidyl, piperazinyl, 4-(alkyl)piperazinyl, pyrrolidinyl, 2-(alkyl)-2,5-diazabicyclo[2.2.1]-heptanyl, 2-oxa-5-azabicyclo[2.2.1]heptanyl.

X advantageously represents an $SO_2$ group.

A preferred $R_2$ group is a cycloalkyl or $(C_2-C_6)$alkyl group, more preferably an ethyl, isopropyl or cyclopentyl group.

Even more especially, the invention relates to compounds of formula (I) which are:

4-({4-[6-(4-isopropylpiperazin-1-yl)pyridin-3-yl]phenyl}sulphonyl)morpholine dihydrochloride,
1-isopropyl-4-{5-[4-(piperidin-1-ylsulphonyl)phenyl]pyridin-2-yl}piperazine dihydrochloride,
1-cyclopentyl-4-{5-[4-(piperidin-1-ylsulphonyl)phenyl]pyridin-2-yl}piperazine dihydrochloride,
1-cyclopropyl-4-{5-[4-(piperidin-1-ylsulphonyl)phenyl]pyridin-2-yl}piperazine dihydrochloride,
1-ethyl-4-{5-[4-(piperidin-1-ylsulphonyl)phenyl]pyridin-2-yl}piperazine dihydrochloride,
1-cyclobutyl-4-{5-[4-(piperidin-1-ylsulphonyl)phenyl]pyridin-2-yl}piperazine dihydrochloride,
1-(5-{4-[(4,4-difluoropiperidin-1-yl)sulphonyl]phenyl}pyridin-2-yl)-4-isopropyl piperazine dihydrochloride,
4-({4-[6-(4-cyclopropylpiperazin-1-yl)pyridin-3-yl]phenyl}sulphonyl)morpholine dihydrochioride,
1-isopropyl-4-(5-{4-[(4-methylpiperazin-1-yl)sulphonyl]phenyl}pyridin-2-yl)piperazine trihydrochloride,
4-({4-[6-(4-isopropylpiperazin-1-yl)pyridin-3-yl]phenyl}sulphonyl)thiomorpholine dihydrochloride,
1-cyclopentyl-4-{5-[4-(phenylsulphonyl)phenyl]pyridin-2-yl}piperazine dihydrochloride,
1-cyclopentyl-4-{5-[3-(piperidin-1-ylsulphonyl)phenyl]pyridin-2-yl}piperazine dihydrochloride,
1-isopropyl-4-{5-[4-(pyrrolidin-1-ylsulphonyl)phenyl]pyridin-2-yl}piperazine dihydrochloride,
4-[6-(4-isopropylpiperazin-1-yl)pyridin-3-yl]-N,N-dimethylbenzenesulphonamide dihydrochloride,
N-cyclopentyl-4-[6-(4-isopropyl-1-piperazinyl)-3-pyridinyl]benzenesulphonamide,
1-cyclopentyl-4 {-5-[4-(piperidin-1-ylcarbonyl)phenyl]pyridin-2-yl}piperazine dihydrochloride,
1-isopropyl-4-{5-[4-(piperidin-1-ylcarbonyl)phenyl]pyridin-2-yl}piperazine dihydrochloride,
1-methyl-4-{5-[4-(piperidin-1-ylsulphonyl)phenyl]pyridin-2-yl}piperazine dihydrochloride,
N-cyclopropyl-4-[6-(4-isopropylpiperazin-1-yl)pyridin-3-yl]benzenesulphonamide dibydrochloride,
N-(tert-butyl)-4-[6-(4-isopropylpiperazin-1-yl)pyridin-3-yl]benzenesulphonamide dihydrochloride,
4-({4-[6-(4-isobutylpiperazin-1-yl)pyridin-3-yl]phenyl}sulphonyl)morpholine dihydrochloride,
1-isopropyl-4-({4-[6-(4-isopropylpiperazin-1-yl)pyridin-3-yl]phenyl}sulphonyl)-piperazine trihydrochloride,
4-[6-(4-isopropylpiperazin-1-yl)pyridin-3-yl]benzenesulphonamide dihydrochloride,
4-({4-[6-(4-isopropylpiperazin-1-yl)pyridin-3-yl]phenyl}sulphonyl)thiomorpholine 1,1-dioxide dihydrochloride,
1-ethyl-4-({4-[6-(4-isopropylpiperazin-1-yl)pyridin-3-yl]phenyl}sulphonyl)piperazine trihydrochloride,
4-({4-[6-(4-isopropylpiperazin-1-yl)pyridin-3yl]phenyl}sulphonyl)thiomorpholine 1-oxide dihydrochloride,
1-{5-[4-(aziridin-1-ylsulphonyl)phenyl]pyridin-2-yl}-4-isopropylpiperazine dihydrochloride,
1-isopropyl-4-(5-{4-[(2-methylpyrrolidin-1-yl)sulphonyl]phenyl}pyridin-2-yl)piperazine dihydrochloride,
1-isopropyl-4-{5-[4-(piperazin-1-ylsulphonyl)phenyl]pyridin-2-yl}piperazine trihydrochloride,
1-cyclohexyl-4-({4-[6-(4-isopropylpiperazin-1-yl)pyridin-3-yl]phenyl}sulphonyl)-piperazine dihydrochloride,
1-({4-[6-(4-isopropylpiperazin-1-yl)pyridin-3-yl]phenyl}sulphonyl)piperidin-4-one dihydrochloride,
1-isopropyl-4-(5-{4-[(2-methylpyrrolidin-1-yl)sulphonyl]phenyl}pyridin-2-yl)piperazine dihydrochloride, enantiomer 1,
1-isopropyl-4-(5-{4-[(2-methylpyrrolidin-1-yl)sulphonyl]phenyl}pyridin-2-yl)piperazine dihydrochloride, enantiomer 2,
2-({4-[6-(4-isopropylpiperazin-1-yl)pyridin-3-yl]phenyl}sulphonyl)-5-methyl-2,5-diazabicyclo[2.2.1]heptane,
1-({4-[6-(4-isopropylpiperazin-1-yl)pyridin-3-yl]phenyl}sulphonyl)-N,N-dimethyl-piperidin-4-amine trihydrochloride,
1-cyclopentyl-4-(5-{4-[(4-methylpiperazin-1-yl)sulphonyl]phenyl}pyridin-2-yl)-piperazine trihydrochloride,
1-({4-[6-(4-isopropylpiperazin-1-yl)pyridin-3-yl]phenyl}sulphonyl)piperidin-4-ol dihydrochloride,
1-isopropyl-4-(5-{3-[(4-methylpiperazin-1-yl)sulphonyl]phenyl}pyridin-2-yl)piperazine trihydrochloride,
1-(5-{4-[(4-fluoropiperidin-1-yl)sulphonyl]phenyl}pyridin-2-yl)-4-isopropylpiperazine dihydrochloride,
4-{4-[6-(4-isopropylpiperazin-1-yl)pyridin-3-yl]benzoyl}morpholine dihydrochloride,
1-isopropyl-4-(5-{4-[(4-methylpiperazin-1-yl)carbonyl]phenyl}pyridin-2-yl)piperazine trihydrochloride,
1-({4-[6-(4-isopropylpiperazin-1-yl)pyridin-3-yl]phenyl}sulphonyl)-N-methylpiperidin-4-amine trihydrochloride,
(1S,4S)-5-({4-[6-(4-isopropylpiperazin-1-yl)pyridin-3-yl]phenyl}sulphonyl)-2-oxa-5-azabicyclo[2.2.1]heptane dihydrochloride,
1-({4-[6-(4-isopropylpiperazin-1-yl)pyridin-3-yl]phenyl}sulphonyl)piperidin-4-amine trihydrochloride.

The invention relates also to a process for the preparation of compounds of formula (I), which process is characterised in that there is used, as starting material, the compound of formula (II):

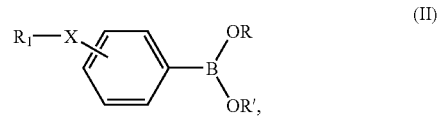

wherein $R_1$ and X are as defined for formula (I), and R and R', which may be the same or different, each represent a hydrogen atom or a linear or branched $(C_1-C_6)$alkyl group or together form a linear or branched $(C_1-C_6)$alkylene chain, which is condensed, in the presence of palladium(0), with a compound of formula (III):

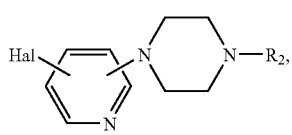

wherein $R_2$ is as defined for formula (I) and Hal represents a halogen atom, to yield the compound of formula (I), which compound of formula (I) is purified, if necessary, according to a conventional purification technique, is separated, where appropriate, into its isomers according to a conventional separation technique and is converted, if desired, into its addition salts with a pharmaceutically acceptable acid or base.

The compounds of formulae (II) and (III) as defined hereinbefore are either commercially available or obtained by conventional reactions of organic chemistry.

By virtue of their pharmacological properties as $H_3$ histamine receptor ligands, the compounds of the present invention are useful in the treatment of cognitive deficiencies associated with cerebral ageing and with neurodegenerative diseases, such as Alzheimer's disease, Parkinson's disease, Pick's disease, Korsakoff's disease and frontal or sub-cortical dementias of vascular or other origin, and also in the treatment of mood disorders, convulsive attacks, attention deficit hyperactivity syndrome, obesity, pain and narcoleptic states.

The present invention relates also to pharmaceutical compositions comprising as active ingredient at least one compound of formula (I), an isomer thereof or an addition salt thereof with a pharmaceutically acceptable acid or base, alone or in combination with one or more inert, non-toxic, pharmaceutically acceptable excipients or carriers.

Among the pharmaceutical compositions according to the invention, there may be mentioned more especially those that are suitable for oral, parenteral (intravenous, intramuscular or subcutaneous), per- or trans-cutaneous, intravaginal, rectal, nasal, perlingual, buccal, ocular or respiratory administration.

The pharmaceutical compositions according to the invention for parenteral injections especially include aqueous and non-aqueous sterile solutions, dispersions, suspensions or emulsions as well as sterile powders for the reconstitution of injectable solutions or dispersions.

The pharmaceutical compositions according to the invention for solid oral administration especially include tablets or dragees, sublingual tablets, sachets, capsules and granules, and for liquid oral, nasal, buccal or ocular administration especially include emulsions, solutions, suspensions, drops, syrups and aerosols.

The pharmaceutical compositions for rectal or vaginal administration are preferably suppositories, and those for per- or trans-cutaneous administration especially include powders, aerosols, creams, ointments, gels and patches.

The above-mentioned pharmaceutical compositions illustrate the invention but do not limit it in any way.

Among the inert, non-toxic, pharmaceutically acceptable excipients or carriers there may be mentioned, without implying any limitation, diluents, solvents, preservatives, wetting agents, emulsifiers, dispersants, binders, swelling agents, disintegrants, retardants, lubricants, absorbency agents, suspension agents, colourants, flavourings etc.

The useful dosage varies according to the age and weight of the patient, the route of administration, the pharmaceutical composition used, the nature and severity of the disorder, and whether any associated treatments are being taken. The dosage ranges from 10 mg to 1 g per day in one or more administrations.

The following Preparations and Examples illustrate the invention but do not limit it in any way.

The starting materials used are known products or are prepared according to known procedures.

The structures of the compounds described in the Examples were determined in accordance with the usual spectrophotometric techniques (infrared, NMR, mass spectrometry etc.).

Preparation 1

1-(5-Bromopyridin-2-yl)-4-isopropylpiperazine

A solution containing 12.1 g of 2,5-dibromopyridine (51.1 mmol), 8.8 ml of 1-isopropyl-piperazine (61.5 mmol) and 9.2 ml of DBU (61.5 mmol) is stirred overnight at 100° C. The reaction mixture is returned to ambient temperature and the solution is diluted with water and extracted with ethyl acetate. The organic phases are collected, washed with brine, dried (MgSO$_4$) and evaporated under reduced pressure. The residue is chromatographed on an SiO$_2$ column, eluting with a mixture of CH$_2$Cl$_2$/MeOH 98/2 and then 96/4, to yield the title product.

Melting point: 76-78° C.

Elemental Microanalysis:

|  | C | H | N | Br |
| --- | --- | --- | --- | --- |
| %, theory | 50.72 | 6.38 | 14.79 | 28.12 |
| %, experiment | 50.96 | 6.47 | 14.53 | 28.33 |

Preparation 2

1-(5-Bromopyridin-2-yl)-4-cyclopentylpiperazine

Identical procedure to that of Preparation 1, but the 1-isopropylpiperazine is replaced by 1-cyclopentylpiperazine.

Melting point: 127-128° C.

Preparation 3

1-(5-Bromopyridin-2-yl)-4-cyclopropylpiperazine

Identical procedure to that of Preparation 1, but the 1-isopropylpiperazine is replaced by 1-cyclopropylpiperazine.

Melting point: 110-115° C.

Preparation 4

1-(5-Bromopyridin-2-yl)-4-ethylpiperazine

Identical procedure to that of Preparation 1, but the 1-isopropylpiperazine is replaced by 1-ethylpiperazine.

Melting point: 66° C.
Elemental Microanalysis:

|              | C     | H    | N     |
|--------------|-------|------|-------|
| %, theory    | 48.90 | 5.97 | 15.55 |
| %, experiment| 48.98 | 6.19 | 15.07 |

Preparation 5

1-(5-Bromopyridin-2-yl)-4-cyclobutylpiperazine

Identical procedure to that of Preparation 1, but the 1-isopropylpiperazine is replaced by 1-cyclobutylpiperazine.
Melting point: 98-102° C.

Preparation 6

1-(5-Bromo-2-pyridinyl)-4-methylpiperazine

Identical procedure to that of Preparation 1, but the 1-isopropylpiperazine is replaced by 4-methylpiperazine.
Melting point: 71-73° C.

Preparation 7

1-(5-Bromo-2-pyridinyl)-4-isobutylpiperazine

Identical procedure to that of Preparation 1, but the 1-isopropylpiperazine is replaced by 1-isobutylpiperazine.
Melting point: 80° C.
Elemental Microanalysis:

|              | C     | H    | N     | Br    |
|--------------|-------|------|-------|-------|
| %, theory    | 52.36 | 6.76 | 14.09 | 26.79 |
| %, experiment| 52.28 | 6.87 | 13.63 | 26.41 |

EXAMPLE 1

4-({4-[6(4-Isopropylpiperazin-1-yl)pyridin-3-yl]phenyl}sulphonyl)-morpholine dihydrochloride Step A: 4-[(4-Iodophenyl)sulphonyl]morpholine To a solution of 50 g of 4-iodobenzenesulphonyl chloride (0.165 mol) in 500 ml of $CH_2Cl_2$ there are added 46 ml of triethylamine (0.33 mol) and then, dropwise, 17 ml of morpholine (0.198 mol). Because the reaction is exothermic, the flask is placed in an ice bath until it has returned to ambient temperature. The reaction mixture is stirred for 1 hour at ambient temperature. After washing the reaction mixture with about 100 ml of 1N HCl and then 100 ml of water, the organic phase is dried ($MgSO_4$) and evaporated under reduced pressure. The solid residue thereby obtained is re-suspended in a small amount of isopropyl ether to yield the title product after filtration and drying in vacuo.
Melting point: 141-144° C.

Step B: [4-(Morpholin4-ylsulphonyl)phenyl]boronic acid

To a solution of 25 g of the compound obtained in Step A (70.8 mmol) and 26 ml of triisopropyl borate in 400 ml of THF cooled to −60° C. there are added, dropwise, over 45 minutes and under a gentle current of nitrogen, 53 ml of a 1.6M solution of BuLi (84.9 mmol) in hexane. The reaction solution is then stirred for 1 hour 30 minutes at −60° C. and is subsequently returned to ambient temperature over 2 hours. The reaction mixture is treated with about 100 ml of 1N HCl and is extracted 3 times with ethyl acetate. The organic phases are collected, washed with brine, dried ($MgSO_4$) and evaporated under reduced pressure. The residue obtained is chromatographed on an $SiO_2$ column, eluting with $CH_2Cl_2$ and then with a mixture of $CH_2Cl_2$/MeOH 98/2 and then 95/5. After evaporation of the fractions, the residue is triturated in ethyl ether to yield the title product after filtration.
Melting point: 104-110° C.

Step C: 4-({4-[6-(4-Isopropylpiperazin-1-yl)pyridin-3-yl]phenyl}sulphonyl)-morpholine dihydrochloride 10.88 g of the compound obtained in Preparation 1 (38.3 mmol), 13.5 g of the compound obtained in Step B (49.8 mmol), 250 ml of dioxane and 190 ml of 0.4M $Na_2CO_3$ in water are introduced into a three-necked flask. The reaction mixture is degassed by bubbling nitrogen through over 30 minutes. Pd(0) tetrakistriphenylphosphine (2.21 g, 1.91 mmol) is introduced and the reaction mixture is stirred at 100° C. under a gentle current of nitrogen for 3 hours. After cooling to ambient temperature, the reaction mixture is diluted with water and extracted with ethyl ether. In the course of the extraction a precipitate forms, which is filtered off, rinsed with water and a small amount of ethyl acetate to yield, after drying in vacuo, a first batch of the title product in the form of the base. The extracted phases are combined with the filtrate, and the organic phase is separated off and then washed with brine. The organic phase is dried ($MgSO_4$) and evaporated under reduced pressure. The evaporation residue is re-suspended in ethanol and filtered off to yield, after drying in vacuo, a second batch of the title compound in the form of the base. The 2 batches are combined and suspended in ethanol. Ethereal HCl is added and the suspension is filtered to yield the title product.
Melting point: 254-256° C.
Elemental Microanalysis:

|              | C     | H    | N     | S    | Cl    |
|--------------|-------|------|-------|------|-------|
| %, theory    | 52.48 | 6.41 | 11.13 | 6.37 | 14.08 |
| %, experiment| 52.62 | 6.40 | 10.93 | 6.50 | 14.45 |

EXAMPLE 2

1-Isopropyl-4-{5-[4-(piperidin-1-ylsulphonyl)phenyl]pyridin-2-yl})-piperazine dihydrochloride Step A: 1-[(4-Iodophenyl)sulphonyl]piperidine Identical procedure to Step A of Example 1, but the morpholine is replaced by piperidine.
Elemental Microanalysis:

|              | C     | H    | N    | S    | I     |
|--------------|-------|------|------|------|-------|
| %, theory    | 37.62 | 4.02 | 3.99 | 9.13 | 36.13 |
| %, experiment| 37.91 | 4.08 | 4.01 | 8.98 | 36.54 |

Step B: [4-(Piperidin-1-ylsulphonyl)phenyl]boronic acid

Identical procedure to Step B of Example 1, starting from the product obtained in Step A.

Melting point: 110° C.

Step C: 1-Isopropyl-4-{5-[4-(piperidin-1-ylsulphonyl)phenyl]pyridin-2-yl}-piperazine dihydrochloride Identical procedure to Step C of Example 1, starting from the product obtained in Step B.

Melting point: 249-252° C.

Elemental Microanalysis:

|  | C | H | N | S | Cl |
|---|---|---|---|---|---|
| %, theory | 55.08 | 6.83 | 11.17 | 6.39 | 14.14 |
| %, experiment | 54.83 | 7.00 | 11.05 | 6.18 | 13.74 |

EXAMPLE 3

1-Cyclopentyl4-{5-[4-(piperidin-1-ylsulphonyl)phenyl]pyridin-2-yl}-piperazine dihydrochloride Identical procedure to Step C of Example 2, but the product of Preparation 1 is replaced by the product obtained in Preparation 2.

Melting point: 241-243° C.

Elemental Microanalysis:

|  | C | H | N | S | Cl |
|---|---|---|---|---|---|
| %, theory | 56.92 | 6.88 | 10.62 | 6.08 | 13.44 |
| %, experiment | 56.65 | 7.11 | 10.37 | 6.13 | 13.07 |

EXAMPLE 4

1-Cyclopropyl4-{5-[4-(piperidin-1-ylsulphonyl)phenyl]pyridin-2-yl}-piperazine dihydrochloride The product of Step B of Example 2 is reacted with the compound obtained in Preparation 3, under the conditions described in Step C of Example 1.

Melting point: 204-208° C.

Elemental Microanalysis:

|  | C | H | N | S | Cl |
|---|---|---|---|---|---|
| %, theory | 55.31 | 6.46 | 11.22 | 6.42 | 14.20 |
| %, experiment | 56.01 | 6.74 | 11.14 | 5.81 | 13.99 |

EXAMPLE 5:

1-Ethyl-4-{5-[4-(piperidin-1-ylsulphonyl)phenyl]pyridin-2-yl}piperazine dihydrochloride The product obtained in Step B of Example 2 is reacted with the compound obtained in Preparation 4, under the conditions described in Step C of Example 1.

Melting point: 245-247° C.

Elemental Microanalysis:

|  | C | H | N | S | Cl |
|---|---|---|---|---|---|
| %, theory | 54.20 | 6.62 | 11.49 | 6.58 | 14.54 |
| %, experiment | 54.87 | 7.01 | 11.56 | 6.12 | 14.92 |

EXAMPLE 6

1-Cyclobutyl-4-{5-[4-(piperidin-1-ylsulphonyl)phenyl]pyridin-2-yl}-piperazine dihydrochloride The product obtained in Step B of Example 2 is reacted with the compound obtained in Preparation 5, under the conditions described in Step C of Example 1.

Melting point: 250-253° C.

Elemental Microanalysis:

|  | C | H | N | S | Cl |
|---|---|---|---|---|---|
| %, theory | 57.77 | 6.79 | 11.23 | 6.43 | 13.81 |
| %, experiment | 57.54 | 6.84 | 11.00 | 6.04 | 11.69 |

EXAMPLE 7

1-(5-{4-[(4,4-Difluoropiperidin-1-yl)sulphonyl]phenyl})pyridin-2-yl)-4-isopropylpiperazine dihydrochloride Step A: 4,4-Difluoro-1-[(4-iodophenyl)sulphonyl]piperidine Identical procedure to Step A of Example 1, but the morpholine is replaced by 4,4-difluoropiperidine.

Melting point : 148-150° C.

Elemental Microanalysis:

|  | C | H | N | S | I |
|---|---|---|---|---|---|
| %, theory | 34.12 | 3.12 | 3.62 | 8.28 | 32.78 |
| %, experiment | 34.62 | 3.27 | 3.66 | 8.30 | 33.36 |

Step B: {4-[(4,4-Difluoropiperidin-1-yl)sulphonyl]phenyl}boronic acid

Identical procedure to Step B of Example 1, starting from the product obtained in Step A.

Melting point: 289° C.

Step C: 1-(5-{4-[(4,4-Difluoropiperidin-1-yl)sulphonyl]phenyl}pyridin-2-yl)-4-isopropylpiperazine dihydrochloride Identical procedure to Step C of Example 1, using the product obtained in Step B.

Melting point: 260-262° C.

Elemental Microanalysis:

|  | C | H | N | S | Cl |
|---|---|---|---|---|---|
| %, theory | 51.4 | 6.00 | 10.42 | 5.97 | 13.19 |
| %, experiment | 51.07 | 5.85 | 10.03 | 6.07 | 13.84 |

EXAMPLE 8

4-({4-[6-(4-Cyclopropylpiperazin-1-yl)pyridin-3-yl]phenyl}sulphonyl)-morpholine dihydrochloride The product of Step B of Example 1 is reacted with the compound obtained in Preparation 3, under the conditions described in Step C of Example 1.

Melting point: 220° C.

Elemental Microanalysis:

|  | C | H | N | S | Cl |
|---|---|---|---|---|---|
| %, theory | 52.69 | 6.03 | 11.17 | 6.39 | 14.14 |
| %, experiment | 52.67 | 6.04 | 10.83 | 6.35 | 14.22 |

EXAMPLE 9

1-Isopropyl-4-(5-{4-[(4-methylpiperazin-1-yl)sulphonyl]phenyl}pyridin-2-yl)piperazine trihydrochloride Step A: 1-[(4-Iodophenyl)sulphonyl]-4-methylpiperazine Identical procedure to Step A of Example 1, but the morpholine is replaced by 4-methyl-piperazine.

Melting point: 181-182° C.

Step B: 1-Methyl-4-{[4-(4,4,5,5-tetramethyl-1,3,2-dioxaborolan-2-yl)phenyl]-sulphonyl}piperazine 5.4 g of the compound obtained in Step A (14.75 mmol), 4.52 g of bis(pinacolato)diborane (19.18 mmol), 4.34 g of potassium acetate (44.25 mmol) and 50 ml of dimethylformamide are introduced into a 100 ml two-necked flask. The reaction mixture is degassed by bubbling a current of nitrogen through for 30 minutes; 165 mg of palladium acetate (0.737 mmol) are then added. The reaction mixture is stirred under a gentle current of nitrogen for 2 hours 30 minutes at 85° C. After cooling to ambient temperature, the reaction mixture is diluted with water and extracted with $CH_2Cl_2$. The organic phases are collected, washed with brine, dried and evaporated under reduced pressure. The residue obtained is chromatographed on $SiO_2$ ($CH_2Cl_2$/MeOH 95/5) to yield the title product in the form of a creamy-white solid.

Melting point: 126-136° C.

Step C: 1-Isopropyl-4-(5-{4-[(4-methylpiperazin-1-yl)sulphonyl]phenyl}pyridin-2-yl)piperazine trihydrochloride Identical procedure to Step C of Example 1, starting from the product obtained in Step B above.

Melting point: 254-258° C.

Elemental Microanalysis:

|  | C | H | N | S | Cl |
|---|---|---|---|---|---|
| %, theory | 49.96 | 6.56 | 12.66 | 5.80 | 19.23 |
| %, experiment | 50.57 | 6.55 | 12.50 | 5.82 | 18.50 |

EXAMPLE 10

4-({4-[6(4-Isopropylpiperazin-1-yl)pyridin-3-yl]phenyl}sulphonyl)-thiomorpholine dihydrochloride Step A: 4-[(4-Iodophenyl)sulphonyl]thiomorpholine Identical procedure to Step A of Example 1, but the morpholine is replaced by thiomorpholine.

Melting point: 131° C.

Step B: [4-(Thiomorpholin-4-ylsulphonyl)phenyl]boronic acid

Identical procedure to Step B of Example 1, starting from the product obtained in Step A.

Melting point: >300° C.

Step C: 4-({4-[6(4-Isopropylpiperazin-1-yl)pyridin-3-yl]phenyl}sulphonyl)-thiomorpholine dihydrochloride Identical procedure to Step C of Example 1, starting from the product obtained in Step B.

Melting point: 248-253° C.

Elemental Microanalysis:

|  | C | H | N | S | Cl |
|---|---|---|---|---|---|
| %, theory | 50.86 | 6.21 | 10.78 | 12.34 | 13.65 |
| %, experiment | 51.51 | 6.41 | 10.35 | 11.74 | 13.95 |

EXAMPLE 11

1-Cyclopentyl-4-{5-[4-(phenylsulphonyl)phenyl]pyridin-2-yl}piperazine dihydrochloride Step A: 1-Bromo-4-(phenylsulphonyl)benzene To a solution of 199 µl of bromobenzene (1.88 mmol) and 361 µl of benzenesulphonyl chloride (2.83 mmol) in 4 ml of trifluoroacetic acid there are added, in succession, 83 mg of indium chloride (0.376 mmol) and then, dropwise, 25 µl of trifluoromethanesulphonic acid. The reaction mixture is stirred for 2 hours at 70° C. and is then returned to ambient temperature and diluted with ice-cold water. After rendering alkaline to pH 10 by adding concentrated sodium hydroxide solution, the reaction mixture is extracted with $CH_2Cl_2$. The organic phases are collected, washed with saturated NaCl, dried ($MgSO_4$) and evaporated under reduced pressure to yield the title product in the form of a white solid.

Melting point: 95-99° C.

Elemental Microanalysis:

|  | C | H | S | Br |
|---|---|---|---|---|
| %, theory | 48.50 | 3.05 | 10.79 | 26.89 |
| %, experiment | 48.21 | 3.21 | 11.17 | 27.32 |

Step B: [4-(Phenylsulphonyl)phenyl]boronic acid

Identical procedure to Step B of Example 1, starting from the product obtained in Step A.

Melting point: 287-290° C.

Step C: 1-Cyclopentyl-4-{5-[4-(phenylsulphonyl)phenyl]pyridin-2-yl}piperazine dihydrochloride Identical procedure to Step C of Example 1, starting from the product obtained in Step B and replacing the product of Preparation 1 by the product of Preparation 2.

Melting point: 155-159° C.
Elemental Microanalysis:

|  | C | H | N | S | Cl |
|---|---|---|---|---|---|
| %, theory | 59.99 | 6.00 | 8.07 | 6.16 | 13.62 |
| %, experiment | 60.36 | 5.86 | 7.95 | 5.99 | 13.99 |

EXAMPLE 12

1-Cyclopentyl-4-{5-[3-(piperidin-1-ylsulphonyl)phenyl]pyridin-2-yl}-piperazine dihydrochloride Step A: 1-[(3-Bromophenyl)sulphonyl]piperidine Identical procedure to Step A of Example 1, starting from 3-bromobenzenesulphonyl chloride and piperidine.

Melting point: 87° C.
Elemental Microanalysis:

|  | C | H | N | S | Br |
|---|---|---|---|---|---|
| %, theory | 43.43 | 4.64 | 4.60 | 10.54 | 26.27 |
| %, experiment | 43.71 | 4.75 | 4.72 | 11.02 | 26.37 |

Step B: [3-(Piperidin-1-ylsulphonyl)phenyl]boronic acid

Identical procedure to Step B of Example 1, starting from the product obtained in Step A.

Melting point: 115-119° C.

Step C: 1-Cyclopentyl-4-{5-[3-(piperidin-1-ylsulphonyl)phenyl]pyridin-2-yl}-piperazine dihydrochloride Identical procedure to Step C of Example 1, starting from the product obtained in Step B and replacing the compound of Preparation 1 by the compound obtained in Preparation 2.

Melting point : 229-231° C.
Elemental Microanalysis:

|  | C | H | N | S | Cl |
|---|---|---|---|---|---|
| %, theory | 56.92 | 6.88 | 10.62 | 6.08 | 13.44 |
| %, experiment | 56.76 | 6.92 | 10.42 | 5.91 | 13.47 |

EXAMPLE 13

1-Isopropyl-4-{5-[4-(pyrrolidin-1-ylsulphonyl)phenyl]pyridin-2-yl}-piperazine dihydrochloride Step A : 1-[(4-Iodophenyl)sulphonyl]pyrrolidine Identical procedure to Step A of Example 1, but the morpholine is replaced by pyrrolidine.

Melting point: 126° C.
Elemental Microanalysis:

|  | C | H | N | S | I |
|---|---|---|---|---|---|
| %, theory | 35.62 | 3.59 | 4.15 | 9.51 | 37.64 |
| %, experiment | 37.13 | 3.80 | 4.19 | 9.29 | 36.89 |

Step B: [4-(Pyrrolidin-1-ylsulphonyl)phenyl]boronic acid

Identical procedure to Step B of Example 1, starting from the product obtained in Step A.

Melting point: 306° C.

Step C: 1-Isopropyl-4-{5-[4-(pyrrolidin-1-ylsulphonyl)phenyl]pyridin-2-yl}-piperazine dihydrochloride Identical procedure to Step C of Example 1, starting from the product obtained in Step B.

Melting point: 240° C.
Elemental Microanalysis:

|  | C | H | N | S | Cl |
|---|---|---|---|---|---|
| %, theory | 54.20 | 6.62 | 11.49 | 6.58 | 14.54 |
| %, experiment | 54.32 | 6.54 | 11.18 | 6.57 | 15.23 |

EXAMPLE 14

4-[6(4-Isopropylpiperazin-1-yl)pyridin-3-yl]-N,N-dimethylbenzene-sulphonamide dihydrochloride Step A: 4-Iodo-N,N-dimethylbenzenesulphonamide Identical procedure to Step A of Example 1, but the morpholine is replaced by dimethylamine.

Melting point: 128° C.
Elemental Microanalysis:

|  | C | H | N | S | I |
|---|---|---|---|---|---|
| %, theory | 30.88 | 3.24 | 4.50 | 10.31 | 40.79 |
| %, experiment | 31.56 | 3.32 | 4.41 | 10.10 | 39.50 |

Step B: {4-[(Dimethylamino)sulphonyl]phenyl}boronic acid

Identical procedure to Step B of Example l, starting from the product obtained in Step A.

Melting point: 306° C.

Step C: 4-[6-(4-Isopropylpiperazin-1-yl)pyridin-3-yl]-N,N-dimethylbenzene-sulphonamide dihydrochloride Identical procedure to Step C of Example 1, starting from the compound obtained in Step B.

Melting point: 240° C.
Elemental Microanalysis:

|  | C | H | N | S | Cl |
|---|---|---|---|---|---|
| %, theory | 52.06 | 6.55 | 12.14 | 6.95 | 15.52 |
| %, experiment | 52.39 | 6.68 | 11.69 | 6.91 | 15.74 |

EXAMPLE 15

N-Cyclopentyl-4-[6(4-isopropyl-1-piperazinyl)-3-pyridinyl]benzene-sulphonamide dihydrochloride Step A: N-Cyclopentyl-4-iodobenzenesulphonamide
Identical procedure to Step A of Example 1, but the morpholine is replaced by cyclopentylamine.

Step B: N-Cyclopentyl-4-(4,4,5,5-tetramethyl-1,3,2-dioxaborolan-2-yl)-benzenesulphonamide
Identical procedure to Step B of Example 9, starting from the product obtained in Step A.

Step C: N-Cyclopentyl-4-[6-(4-isopropyl-1-piperazinyl)-3-pyridinyl]benzene-sulphonamide dihydrochloride
Identical procedure to Step C of Example 1, starting from the compound obtained in Step B.

EXAMPLE 16

1-Cyclopentyl-4-{5-[4-(piperidin-1-ylcarbonyl)phenyl]pyridin-2-yl}-piperazine dihydrochloride Step A: 1-(4-Iodobenzoyl)piperidine
To a suspension of 4.0 g of 4-iodobenzoic acid (16.13 mmol) in 40 ml of $CH_2Cl_2$ there are added 3.65 ml of diisopropylethylamine (20.97 mmol) and then, after 10 minutes, 5.18 g of TBTU (16.13 mmol). After stirring for 10 minutes more, 1.60 ml of piperidine (16.13 mmol) are added and the reaction mixture is stirred overnight at ambient temperature. The reaction mixture is washed 3 times with water and then once with saturated NaCl. After drying ($MgSO_4$) and evaporation under reduced pressure, the residue is chromatographed on silica ($CH_2Cl_2$/acetone 9/1) to yield the title product.
Melting point :115-118° C.

Step B: [4-(Piperidin-1-ylcarbonyl)phenyl]boronic acid
Identical procedure to Step B of Example 1, starting from the compound obtained in Step A.
Melting point: 135-140° C.

Step C: 1-Cyclopentyl-4-{5-[4-(piperidin-1-ylcarbonyl)phenyl]pyridin-2-yl}-piperazine dihydrochloride
Identical procedure to Step C of Example 1, starting from the compound obtained in Step B and the compound obtained in Preparation 2.
Melting point: 227-230° C.
Elemental Microanalysis:

|  | C | H | N | Cl |
|---|---|---|---|---|
| %, theory | 63.54 | 7.38 | 11.40 | 14.43 |
| %, experiment | 63.45 | 7.42 | 11.31 | 14.46 |

EXAMPLE 17

1-Isopropyl-4-{5-[4-(piperidin-1-ylcarbonyl)phenyl]pyridin-2-yl})-piperazine dihydrochloride Identical procedure to Step C of Example 16, but the product obtained in Preparation 2 is replaced by the compound obtained in Preparation 1.

Melting point: 240-243° C.
Elemental Microanalysis:

|  | C | H | N | Cl |
|---|---|---|---|---|
| %, theory | 61.93 | 7.36 | 12.04 | 15.23 |
| %, experiment | 62.14 | 7.35 | 11.62 | 15.33 |

EXAMPLE 18

1-Methyl-4-{5-[4-(piperidin-1-ylsulphonyl)phenyl]pyridin-2-yl}-piperazine dihydrochloride The product of Step B of Example 2 is reacted with the compound obtained in Preparation 6, under the conditions described in Step C of Example 1.
Melting point: 250-255° C.
Elemental Microanalysis:

|  | C | H | N | S | Cl |
|---|---|---|---|---|---|
| %, theory | 53.27 | 6.39 | 11.83 | 6.77 | 14.98 |
| %, experiment | 53.51 | 6.40 | 11.82 | 6.71 | 15.16 |

EXAMPLE 19

N-Cyclopropyl-4-[6-(4-isopropylpiperazin-1-yl)pyridin-3-yl]benzene-sulphonamide dihydrochloride Step A: N-Cyclopropyl-4-iodobenzenesulphonamide
Identical procedure to Step A of Example 1, but the morpholine is replaced by cyclopropylamine.

Step B: N-Cyclopropyl-4-(4,4,5,5-tetramethyl-1,3,2-dioxaborolan-2-yl)-benzenesulphonamide
Identical procedure to Step B of Example 9, starting from the product obtained in Step A.
Melting point: 99° C.

Step C: N-Cyclopropyl-4-[6-(4-isopropylpiperazin-1-yl)pyridin-3-yl]benzene-sulphonamide dihydrochloride
Identical procedure to Step C of Example 1, starting from the compound obtained in Step B.
Melting point: 269° C.
Elemental Microanalysis:

|  | C | H | N | S | Cl |
|---|---|---|---|---|---|
| %, theory | 53.27 | 6.39 | 11.83 | 6.77 | 14.98 |
| %, experiment | 53.22 | 6.44 | 11.66 | 6.51 | 14.98 |

EXAMPLE 20

N-(tert-Butyl)-4-[6-(4-isopropylpiperazin-1-yl)pyridin-3-yl]benzene-sulphonamide dihydrochloride Step A: N-(tert-Butyl)-4-iodobenzenesulphonamide
Identical procedure to Step A of Example 1, but the morpholine is replaced by tert-butylamine.
Melting point: 121° C.

Step B: N-(tert-Butyl)-4-(4,4,5,5-tetramethyl-1,3,2-dioxaborolan-2-yl)benzene-sulphonamide
Identical procedure to Step B of Example 9, starting from the product obtained in Step A.

Step C: N-(tert-Butyl)-4-[6-(4-isopropylpiperazin-1-yl)pyridin-3-yl]benzene-sulphonamide dihydrochloride
Identical procedure to Step C of Example 1, starting from the compound obtained in Step B.
Melting point: 215-230° C.
Elemental Microanalysis:

|  | C | H | N | S | Cl |
|---|---|---|---|---|---|
| %, theory | 53.98 | 7.00 | 11.45 | 6.55 | 14.48 |
| %, experiment | 54.19 | 7.05 | 11.16 | 5.25 | 14.52 |

EXAMPLE 21

4-({4-[6-(4-Isobutylpiperazin-1-yl)pyridin-3-yl]phenyl}sulphonyl)-morpholine dihydrochloride The product obtained in Step B of Example I is reacted with the compound obtained in Preparation 7, under the conditions described in Step C of Example 1.
Melting point: 137° C.
Elemental Microanalysis:

|  | C | H | N | S | Cl |
|---|---|---|---|---|---|
| %, theory | 53.76 | 6.65 | 10.90 | 6.24 | 13.11 |
| %, experiment | 54.14 | 6.57 | 10.74 | 6.06 | 13.04 |

EXAMPLE 22

1-Isopropyl-4-({4-[6-(4-isopropylpiperazin-1-yl)pyridin-3-yl]phenyl}-sulphonyl)piperazine trihydrochloride Step A: 1-[(4-Iodophenyl)sulphonyl]-4-isopropylpiperazine
Identical procedure to Step A of Example 1, but the morpholine is replaced by 1-isopropylpiperazine.
Melting point: 139° C.

Step B: 1-Isopropyl-4-{[4-(4,4,5,5-tetramethyl-1,3,2-dioxaborolan-2-yl)-phenyl]sulphonyl}piperazine
Identical procedure to Step B of Example 9, starting from the product obtained in Step A.

Step C: 1-Isopropyl-4-({4-[6-(4-isopropylpiperazin-1-yl)pyridin-3-yl]-phenyl}sulphonyl)piperazine trihydrochloride
Identical procedure to Step C of Example 1, starting from the product obtained in Step B.
Melting point: 290° C.
Elemental Microanalysis:

|  | C | H | N | S | Cl |
|---|---|---|---|---|---|
| %, theory | 51.68 | 6.94 | 12.05 | 5.52 | 18.3 |
| %, experiment | 51.35 | 7.39 | 11.77 | 5.35 | 18.5 |

EXAMPLE 23

4-[6-(4-Isopropylpiperazin-1-yl)pyridin-3-yl]benzenesulphonamide dihydrochloride Step A: 4-Iodobenzenesulphonamide
Identical procedure to Step A of Example 1, but the morpholine is replaced by ammonia gas.
Melting point: 173° C.

Step B: 4-(4,4,5,5-Tetramethyl-1,3,2-dioxaborolan-2-yl)benzenesulphonamide
Identical procedure to Step B of Example 9, starting from the product obtained in Step A.

Step C: 4-[6-(4-Isopropylpiperazin-1-yl)pyridin-3-yl]benzenesulphonamide dihydrochloride
Identical procedure to Step C of Example 1, starting from the product obtained in Step B.
Melting point: 297-301° C.
Elemental Microanalysis:

|  | C | H | N | S | Cl |
|---|---|---|---|---|---|
| %, theory | 49.88 | 6.05 | 12.93 | 7.4 | 16.36 |
| %, experiment | 50.05 | 6.21 | 12.58 | 7.39 | 16.46 |

EXAMPLE 24

4-({4-[6(4-Isopropylpiperazin-1-yl)pyridin-3-yl]phenyl}sulphonyl)-thiomorpholine1,1-dioxide dihydrochloride To a suspension of 400 mg of the product obtained in Example 10 (0.76 mmol) in a mixture of 3 ml of acetone and 12 ml of water there are added 266 mg of 4-methylmorpholine N-oxide (2.27 mmol) and 34 µl of a 2.5% solution of osmium tetroxide in tert-butanol. After stirring for 16 hours at ambient temperature, the reaction mixture is treated with a saturated sodium bisulphite and 10% sodium hydrogen carbonate solution. The mixture is extracted with $CH_2Cl_2$, and the organic phases are dried over $MgSO_4$ and evaporated under reduced pressure. The residue is treated with methanolic HCl to yield, after filtration, the title product in the form of a white solid.
Melting point: 278-280° C.
Elemental Microanalysis:

|  | C | H | N | S | Cl |
|---|---|---|---|---|---|
| %, theory | 47.91 | 5.85 | 10.16 | 11.63 | 12.86 |
| %, experiment | 48.57 | 5.68 | 10.08 | 11.73 | 13.58 |

EXAMPLE 25

1-Ethyl-4-({4-[6(4-isopropylpiperazin-1-yl)pyridin-3-yl]phenyl}-sulphonyl)piperazine trihydrochloride Step A: 1-[(4-Iodophenyl)sulphonyl]-4-ethylpiperazine
Identical procedure to Step A of Example 1, but the morpholine is replaced by 1-ethylpiperazine.

Melting point: 148° C.

Elemental Microanalysis:

|  | C | H | N | S | I |
|---|---|---|---|---|---|
| %, theory | 37.90 | 4.51 | 7.37 | 8.43 | 33.37 |
| %, experiment | 37.74 | 4.50 | 7.16 | 8.22 | 31.85 |

Step B: 1-Ethyl-4-{[4-(4,4,5,5-tetramethyl-1,3,2-dioxaborolan-2-yl)phenyl]-sulphonyl}piperazine Identical procedure to Step B of Example 9, starting from the product obtained in Step A.

Step C: 1-Ethyl-4-({4-[6-(4-isopropylpiperazin-1-yl)pyridin-3-yl]phenyl}-sulphonyl)piperazine trihydrochloride Identical procedure to Step C of Example 1, starting from the product obtained in Step B.

Melting point: 249° C.

Elemental Microanalysis:

|  | C | H | N | S | Cl |
|---|---|---|---|---|---|
| %, theory | 50.84 | 6.75 | 12.35 | 5.66 | 18.76 |
| %, experiment | 50.33 | 6.53 | 11.84 | 5.26 | 18.76 |

EXAMPLE 26

4-({4-[6-(4-Isopropylpiperazin-1-yl)pyridin-3-yl]phenyl}sulphonyl)-thiomorpholine1-oxide dihydrochloride To a solution of 183 ml of $NaIO_4$ (0.86 mmol) in 8 ml of water there are added 424 mg of the product of Example 10, and the reaction mixture is stirred for 1 hour at ambient temperature. The mixture is extracted with $CH_2Cl_2$, and the organic phases are dried over $MgSO_4$. After evaporation under reduced pressure, the residue is treated with methanolic HCl to yield, after filtration, the title product in the form of a white solid.

Melting point: 265° C.

Elemental Microanalysis:

|  | C | H | N | S | Cl |
|---|---|---|---|---|---|
| %, theory | 49.68 | 6.04 | 10.53 | 12.06 | 12.66 |
| %, experiment | 49.91 | 6.14 | 10.03 | 11.95 | 12.39 |

EXAMPLE 27

1-{5-[4(Aziridin-1-ylsulphonyl)phenyl]pyridin-2-yl}isopropyl-piperazine dihydrochloride Step A: 1-Cyclopropyl-4-[(4-iodophenyl)sulphonyl]piperazine Identical procedure to Step A of Example 1, but the morpholine is replaced by 1-cyclopropylpiperazine.

Melting point: 169° C.

Step B: 1-Cyclopropyl-4-{[4-(4,4,5,5-tetramethyl-1,3,2-dioxaborolan-2-yl)-phenyl]sulphonyl}piperazine Identical procedure to Step B of Example 9, starting from the product obtained in Step A.

Step C: 1-Isopropyl-4-({4-[6-(4-isopropylpiperazin-1-yl)pyridin-3-yl]phenyl}-sulphonyl)piperazine trihydrochloride Identical procedure to Step C of Example 1, starting from the product obtained in Step B.

Melting point: 149° C.

Elemental Microanalysis:

|  | C | H | N | S | Cl |
|---|---|---|---|---|---|
| %, theory | 55.34 | 6.87 | 12.91 | 5.91 | 13.07 |
| %, experiment | 55.22 | 7.01 | 12.52 | 5.99 | 12.98 |

EXAMPLE 28

1-Isopropyl-4-(5-{4-[(2-methylpyrrolidin-1-yl)sulphonyl]phenyl}-pyridin-2-yl)piperazine dihydrochloride Step A: :1-[(4-Iodophenyl)sulphonyl]-2-methylpyrrolidine Identical procedure to Step A of Example 1, but the morpholine is replaced by 2-methylpyrrolidine.

Melting point: 76° C.

Step B: {4-[(2-Methylpyrrolidin-1-yl)sulphonyl]phenyl}boronic acid

Identical procedure to Step B of Example 1, starting from the product obtained in Step A.

Melting point: 125-128° C.

Step C: 1-Isopropyl-4-(5-{4-[(2-methylpyrrolidin-1-yl)sulphonyl]phenyl}-pyridin-2-yl)piperazine dihydrochloride Identical procedure to Step C of Example 1, starting from the product obtained in Step A.

Melting point: 208-213° C.

Elemental Microanalysis:

|  | C | H | N | S | Cl |
|---|---|---|---|---|---|
| %, theory | 55.08 | 6.83 | 11.17 | 6.39 | 14.14 |
| %, experiment | 55.27 | 6.77 | 10.95 | 6.27 | 14.47 |

EXAMPLE 29

1-Isopropyl-4-(5-[4-(piperazin-1-ylsulphonyl)phenyl]pyridin-2-yl)-piperazine trihydrochloride Step A: tert-Butyl 4-[(4-iodophenyl)sulphonyl]piperazine-1-carboxylate Identical procedure to Step A of Example 1, but the morpholine is replaced by tert-butyl piperazine-1-carboxylate.

Step B: (4-{[4-(tert-Butoxycarbonyl)piperazin-1-yl]sulphonyl}phenyl)boronic acid Identical procedure to Step B of Example 1, starting from the product obtained in Step A.

Step C: tert-Butyl 4-({4-[6-(4-isopropylpiperazin-1-yl)pyridin-3-yl]phenyl}-sulphonyl)piperazine-1-carboxylate
Identical procedure to Step C of Example 1, starting from the product obtained in Step A.
Melting point: 194° C.

Step D: 1-Isopropyl-4-{5-[4-(piperazin-1-ylsulphonyl)phenyl]pyridin-2-yl}-piperazine trihydrochloride
Deprotection is carried out in a 1/1 mixture of dioxane and methanolic HCl.
Melting point: 265-273° C.
Elemental Microanalysis:

|  | C | H | N | S | Cl |
|---|---|---|---|---|---|
| %, theory | 49.03 | 6.36 | 12.99 | 5.95 | 19.73 |
| %, experiment | 49.63 | 6.49 | 12.86 | 6.2 | 20.39 |

EXAMPLE 30

1-Cyclohexyl-4-({4-[6-(4-isopropylpiperazin-1-yl)pyridin-3-yl]phenyl}-sulphonyl)piperazine dihydrochloride Step A: 1-Cyclohexyl-4-[(4-iodophenyl)sulphonyl]piperazine
Identical procedure to Step A of Example 1, but the morpholine is replaced by 1-cyclohexylpiperazine.
Melting point: 174-177° C.
Elemental Microanalysis:

|  | C | H | N | S | I |
|---|---|---|---|---|---|
| %, theory | 44.25 | 5.34 | 6.45 | 7.38 | 29.22 |
| %, experiment | 44.16 | 5.33 | 6.37 | 7.00 | 29.07 |

Step B: 1-Cyclohexyl-4-{[4-(4,4,5,5-tetramethyl-1,3,2-dioxaborolan-2-yl)-phenyl]sulphonyl}piperazine
Identical procedure to Step B of Example 9, starting from the product obtained in Step A.

Step C: 1-Cyclohexyl-4-({4-[6-(4-isopropylpiperazin-1-yl)pyridin-3-yl]-phenyl}sulphonyl)piperazine dihydrochloride
Identical procedure to Step C of Example 1, starting from the product obtained in Step B.
Melting point: 276-281° C.
Elemental Microanalysis:

|  | C | H | N | S | Cl |
|---|---|---|---|---|---|
| %, theory | 57.52 | 7.41 | 11.98 | 5.48 | 12.13 |
| %, experiment | 58.01 | 7.32 | 12.18 | 5.2 | 12.86 |

EXAMPLE 31

1-({4-[6-(4-Isopropylpiperazin-1-yl)pyridin-3-yl]phenyl}sulphonyl)-piperidin-4-one dihydrochloride Step A: 8-[(4-Iodophenyl)sulphonyl]-1,4-dioxa-8-azaspiro[4.5]decane
Identical procedure to Step A of Example 1, but the morpholine is replaced by 1,4-dioxa-8-azaspiro[4.5]decane.
Melting point: 166-169° C.

Step B: [4-(1,4-Dioxa-8-azaspiro[4.5]dec-8-ylsulphonyl)phenyl]boronic acid
Identical procedure to Step B of Example 1, starting from the product obtained in Step A.
Melting point: 146-148° C.

Step C: 8-({4-[6-(4-Isopropylpiperazin-1-yl)pyridin-3-yl]phenyl}sulphonyl)-1,4-dioxa-8-azaspiro[4.5]decane
Identical procedure to Step C of Example 1, starting from the product obtained in Step B.
Melting point: 215° C.
Elemental Microanalysis:

|  | C | H | N | S |
|---|---|---|---|---|
| %, theory | 61.70 | 7.04 | 11.51 | 6.59 |
| %, experiment | 61.28 | 7.05 | 11.54 | 6.58 |

Step D: 1-({4-[6-(4-Isopropylpiperazin-1-yl)pyridin-3-yl]phenyl}sulphonyl)-piperidin-4-one dihydrochloride
A suspension of 400 mg of the product obtained in Step C (0.82 mmol) in 5 ml of 1N HCl is stirred for 1 hour at 80° C. After neutralisation of the reaction mixture using 10% NaHCO$_3$, the precipitate is filtered off, washed with water and dried. The white solid is suspended in ethanol and dissolved by adding methanolic HCl. The solution is evaporated to dryness and the residue is taken up in an ethanol/ethyl ether mixture to yield the expected product after filtration.
Melting point: >260° C.
Elemental Microanalysis:

|  | C | H | N | S | Cl |
|---|---|---|---|---|---|
| %, theory | 53.59 | 6.26 | 10.87 | 6.22 | 13.75 |
| %, experiment | 54.25 | 6.25 | 10.84 | 6.51 | 13.48 |

EXAMPLE 32

1-Isopropyl-4-(5-{4-[(2-methylpyrrolidin-1-yl)sulphonyl]phenyl}-pyridin-2-yl)piperazine dihydrochloride, enantiomer 1

The 2 enantiomers of the compound described in Example 28 (in the form of the free base) are separated by chiral chromatography on a Chiralpak AD column, using a mixture of methanol/acetonitrile/diethylamine 150/850/1 as eluant. The hydrochlorides are obtained by treatment with methanolic HCl.
Enantiomer 1:
Melting point: 243-247° C.
Elemental Microanalysis:

|  | C | H | N | S | Cl |
|---|---|---|---|---|---|
| %, theory | 55.08 | 6.83 | 11.17 | 6.39 | 14.14 |
| %, experiment | 55.31 | 6.84 | 10.96 | 6.37 | 14.58 |

EXAMPLE 33

1-Isopropyl-4-(5-{4-[(2-methylpyrrolidin-1-yl)sulphonyl]phenyl}-pyridin-2-yl)piperazine dihydrochloride, enantiomer 2

The 2 enantiomers of the compound described in Example 28 (in the form of the free base) are separated by chiral chromatography on a Chiralpak AD column, using a mixture of methanol/acetonitrile/diethylamine 150/850/1 as eluant. The hydrochlorides are obtained by treatment with methanolic HCl.

Enantiomer 2:
Melting point: 245-249° C.
Elemental Microanalysis:

|  | C | H | N | S | Cl |
|---|---|---|---|---|---|
| %, theory | 55.08 | 6.83 | 11.17 | 6.39 | 14.14 |
| %, experiment | 55.41 | 6.75 | 11.12 | 6.32 | 14.85 |

EXAMPLE 34

2-({4-[6-(4-Isopropylpiperazin-1-yl)pyridin-3-yl]phenyl}sulphonyl)-5-methyl-2,5-diazabicyclo [2.2.1] heptane Step A: 2-[(4-Iodophenyl)sulphonyl]-5-methyl-2,5-diazabicyclo[2.2.1]heptane Identical procedure to Step A of Example 1, but the morpholine is replaced by 2-methyl-2,5-diazabicyclo[2.2.1]heptane.

Melting point: 149-152° C.

Step B: 2-Methyl-5-{[4-(4,4,5,5-tetramethyl-1,3,2-dioxaborolan-2-yl)phenyl]-sulphonyl}-2,5-diazabicyclo[2.2.1]heptane Identical procedure to Step B of Example 9, starting from the product obtained in Step A.

Step C: 2-({4-[6-(4-Isopropylpiperazin-1-yl)pyridin-3-yl]phenyl}sulphonyl)-5-methyl-2,5-diazabicyclo[2.2.1]heptane Identical procedure to Step C of Example 1, starting from the product obtained in Step B.

Melting point: 194-198° C.
Elemental Microanalysis:

|  | C | H | N | S |
|---|---|---|---|---|
| %, theory | 63.27 | 7.30 | 15.37 | 7.04 |
| %, experiment | 63.09 | 7.36 | 14.73 | 6.76 |

EXAMPLE 35

1-({4-[6-(4-Isopropylpiperazin-1-yl)pyridin-3-yl]phenyl}sulphonyl)-N,N-dimethylpiperidin-4-amine trihydrochloride To a suspension of 242 mg of the product obtained in Example 32 (0.54 mmol) in 2 ml of ethanol there are added 89 mg of dimethylamine hydrochloride (1.09 mmol), 153 µl of Et₃N (1.09 mmol) and 323 µl of titanium(IV) isopropoxide (1.08 mmol). After stirring for 16 hours at ambient temperature, 52 mg of NaCNBH₄ (0.82 mmol) are added and stirring is continued for 5 hours at ambient temperature. The reaction mixture is treated by addition of 28% ammonium hydroxide solution and the mixture is extracted with CH₂Cl₂. The organic phases are dried over MgSO₄ and, after evaporation under reduced pressure, the residue is purified by chromatography on a silica column, eluting with a 96/4 mixture of CH₂Cl₂/MeOH. The trihydrochloride is obtained by treating the base with methanolic HCl to yield, after filtration, the title product in the form of a white solid.

Melting point: 283-286° C.
Elemental Microanalysis:

|  | C | H | N | S | Cl |
|---|---|---|---|---|---|
| %, theory | 51.68 | 6.94 | 12.05 | 5.52 | 18.3 |
| %, experiment | 51.81 | 7.08 | 12.08 | 4.81 | 17.86 |

EXAMPLE 36

1-Cyclopentyl-4-(5-{4-[(4-methylpiperazin-1-yl)sulphonyl]phenyl}-pyridin-2-yl)piperazine trihydrochloride Step A: tert-Butyl 4-({4-[6-(4-cyclopentylpiperazin-1-yl)pyridin-3-yl]phenyl}-sulphonyl)piperazine-1-carboxylate The product obtained in Step B of Example 29 is reacted with the compound obtained in Preparation 2, under the conditions described in Step C of Example 1.

Melting point: 235-238° C.
Elemental Microanalysis:

|  | C | H | N | S |
|---|---|---|---|---|
| %, theory | 62.68 | 7.44 | 12.60 | 5.77 |
| %, experiment | 62.56 | 7.46 | 12.36 | 5.89 |

Step B: 1-Cyclopentyl-4-{5-[4-(piperazin-1-ylsulphonyl)phenyl]pyridin-2-yl}-piperazine Deprotection is carried out in a 1/1 mixture of dioxane and methanolic HCl. The base is reformed by treatment with 10% NaHCO₃.

Step C: 1-Cyclopentyl-4-(5-{4-[(4-methylpiperazin-1-yl)sulphonyl]phenyl}-pyridin-2-yl)piperazine trihydrochloride A suspension of 500 mg of the product obtained in Step B (1.10 mmol), 270 mg of sodium acetate (3.29 mmol) and 66 mg of paraformaldehyde (2.19 mmol) in 10 ml of ethanol is stirred overnight at ambient temperature. 138 mg of NaCNBH₃ (2.19 mmol), in several portions, are then added to the reaction mixture and stirring is continued for 6 hours at ambient temperature. The reaction mixture is concentrated under reduced pressure, the residue is taken up in 1N HCl and the mixture is stirred for 30 minutes at ambient temperature. The mixture is then rendered alkaline by adding 1N NaOH and the white precipitate that forms is filtered off. The precipitate is re-suspended in warm ethanol and, after adding ethereal HCl, a solution is obtained which results in crystallisation of the title product at ambient temperature.

Melting point: 263-267° C.

Elemental Microanalysis:

|  | C | H | N | S | Cl |
|---|---|---|---|---|---|
| %, theory | 51.86 | 6.61 | 12.09 | 5.54 | 18.37 |
| %, experiment | 52.25 | 6.68 | 11.96 | 5.33 | 18.94 |

EXAMPLE 37

1-({4-[6-(4-Isopropylpiperazin-1-yl)pyridin-3-yl]phenyl}sulphonyl)-piperidin-4-ol dihydrochloride To a suspension of 1 g of the product obtained in Example 32 (2.26 mmol) in 20 ml of methanol there are added, in several portions, 257 mg of $NaBH_4$, and the reaction mixture is stirred for 2 hours at ambient temperature. After adding 40 ml of water, the reaction mixture is extracted with $CH_2Cl_2$, and the organic phases are combined, dried over $MgSO_4$ and evaporated under reduced pressure. The residue is re-suspended in ethanol and filtered off. The solid is dissolved in methanolic HCl, the solution is evaporated to dryness and the residue is triturated in ethyl ether to yield the title product after filtration.

Melting point: 162° C.

Elemental Microanalysis:

|  | C | H | N | S | Cl |
|---|---|---|---|---|---|
| %, theory | 53.38 | 6.62 | 10.83 | 6.2 | 13.7 |
| %, experiment | 53.64 | 6.79 | 10.88 | 6.03 | 12.63 |

EXAMPLE 38

1-Isopropyl-4-(5-{3-[(4-methylpiperazin-1-yl)sulphonyl]phenyl}pyridin-2-yl)piperazine trihydrochloride Step A: tert-Butyl 4-[(3-bromophenyl)sulphonyl]piperazine-1-carboxylate Identical procedure to Step A of Example 1, but the morpholine is replaced by tert-butyl piperazine-1-carboxylate and the 4-iodobenzenesulphonyl chloride by 3-bromobenzenesulphonyl chloride.

Step B: (3-{[4-(tert-Butoxycarbonyl)piperazin-1-yl]sulphonyl}phenyl)boronic acid Identical procedure to Step B of Example 1, starting from the product obtained in Step A.

Melting point: 225° C.

Step C: tert-Butyl 4-({3-[6-(4-isopropylpiperazin-1-yl)pyridin-3-yl]phenyl}-sulphonyl)piperazine-1-carboxylate Identical procedure to Step C of Example 1, starting from the product obtained in Step B.

Step D: 1-Isopropyl-4-{5-[3-(piperazin-1-ylsulphonyl)phenyl]pyridin-2-yl}piperazine Identical procedure to Step B of Example 37, starting from the product obtained in Step C.

Step E: 1-Isopropyl-4-(5-{3-[(4-methylpiperazin-1-yl)sulphonyl]phenyl}pyridin-2-yl)piperazine trihydrochloride Identical procedure to Step C of Example 37, starting from the product obtained in Step D.

Melting point: 168° C.

Elemental Microanalysis:

|  | C | H | N | S | Cl |
|---|---|---|---|---|---|
| %, theory | 49.96 | 6.56 | 12.66 | 5.8 | 19.23 |
| %, experiment | 50.07 | 6.14 | 12.55 | 5.67 | 19.47 |

EXAMPLE 39

1-(5-{4-[(4-Fluoropiperidin-1-yl)sulphonyl]phenyl}pyridin-2-yl)-4-isopropylpiperazine dihydrochloride Step A: 4-Fluoro-1-[(4-iodophenyl)sulphonyl]piperidine Identical procedure to Step A of Example 1, but the morpholine is replaced by 4-fluoropiperidine.

Melting point: 130-133° C.

Step B {4-[(4-Fluoropiperidin-1-yl)sulphonyl]phenyl}boronic acid

Identical procedure to Step B of Example 1, starting from the product obtained in Step A.

Step C: 1-(5-{4-[(4-Fluoropiperidin-1-yl)sulphonyl]phenyl}pyridin-2-yl)-4-isopropylpiperazine dihydrochloride Identical procedure to Step C of Example 1, starting from the product obtained in Step B.

Melting point: 243-247° C.

Elemental Microanalysis:

|  | C | H | N | S | Cl |
|---|---|---|---|---|---|
| %, theory | 53.18 | 6.4 | 10.78 | 6.17 | 13.65 |
| %, experiment | 52.91 | 6.4 | 10.6 | 5.79 | 13.46 |

EXAMPLE 40

4-{4-[6-(4-Isopropylpiperazin-1-yl)pyridin-3-yl]benzoyl}morpholine dihydrochloride Step A: 4-(4-Iodobenzoyl)morpholine Identical procedure to Step A of Example 16, but the piperidine is replaced by morpholine.

Step B: [4-(Morpholin-4-ylcarbonyl)phenyl]boronic acid

Identical procedure to Step B of Example 1, starting from the compound obtained in Step A.

Melting point: 116° C.

Step C: 4-{4-[6-(4-Isopropylpiperazin-1-yl)pyridin-3-yl]benzoyl}morpholine dihydrochloride Identical procedure to Step C of Example 1, starting from the compound obtained in Step B.

Melting point: 224° C.
Elemental Microanalysis:

|  | C | H | N | Cl |
|---|---|---|---|---|
| %, theory | 59.1 | 6.9 | 11.99 | 15.17 |
| %, experiment | 58.68 | 6.91 | 11.6 | 15.05 |

EXAMPLE 41

1-Isopropyl-4-(5-{4-[(4-methylpiperazin-1-yl)carbonyl]phenyl}pyridin-2-yl)piperazine trihydrochloride Step A: 1-(4-Iodobenzoyl)-4-methylpiperazine
Identical procedure to Step A of Example 16, but the piperidine is replaced by 1-methylpiperazine.
Step B: 1-Methyl-4-[4-(4,4,5,5-tetramethyl-1,3,2-dioxaborolan-2-yl)benzoyl]-piperazine
Identical procedure to Step B of Example 9, starting from the product obtained in Step A.
Melting point: 92° C.
Step C: 1-Isopropyl-4-(5-{4-[(4-methylpiperazin-1-yl)carbonyl]phenyl}pyridin-2-yl)piperazine trihydrochloride
Identical procedure to Step C of Example 1, starting from the compound obtained in Step B.
Melting point: 288° C.
Elemental Microanalysis:

|  | C | H | N | Cl |
|---|---|---|---|---|
| %, theory | 55.76 | 7.02 | 13.55 | 20.57 |
| %, experiment | 55.40 | 7.02 | 13.08 | 20.13 |

EXAMPLE 42

1-({4-[6(4-Isopropylpiperazin-1-yl)pyridin-3-yl]phenyl}sulphonyl)-N-methylpiperidin-4-amine trihydrochloride Identical procedure to Example 35, but the dimethylamine hydrochloride is replaced by 2M methylamine in methanol.
Melting point: 284-288° C.
Elemental Microanalysis:

|  | C | H | N | S | Cl |
|---|---|---|---|---|---|
| %, theory | 50.84 | 6.75 | 12.35 | 5.66 | 18.76 |
| %, experiment | 50.87 | 6.81 | 12.13 | 5.23 | 18.91 |

EXAMPLE 43

(1S,4S)-5-({4-[6-(4-Isopropylpiperazin-1-yl)pyridin-3-yl]phenyl}-sulphonyl)-2-oxa-5-azabicyclo[2.2.1]heptane dihydrochloride Step A: (1S,4S)-5-[(4-Iodophenyl)sulphonyl]-2-oxa-5-azabicyclo[2.2.1]heptane
Identical procedure to Step A of Example 1, but the morpholine is replaced by (1S,4S)-2-oxa-5-azabicyclo[2.2.1]heptane.
Melting point: 146-148° C.

Step B: {4-[(1S,4S)-2-Oxa-5-azabicyclo[2.2.1]hept-5-ylsulphonyl]phenyl}-boronic acid
Identical procedure to Step B of Example 1, starting from the product obtained in Step A.

Step C: 1-(5-{4-[(4-Fluoropiperidin-1-yl)sulphonyl]phenyl}pyridin-2-yl)-4-isopropylpiperazine dihydrochloride
Identical procedure to Step C of Example 1, starting from the compound obtained in Step B.
Melting point: 238-242° C.
Elemental Microanalysis:

|  | C | H | N | S | Cl |
|---|---|---|---|---|---|
| %, theory | 53.59 | 6.26 | 10.87 | 6.22 | 13.75 |
| %, experiment | 53.36 | 6.34 | 10.62 | 5.86 | 13.80 |

EXAMPLE 44

1-({4-[6(4-Isopropylpiperazin-1-yl)pyridin-3-yl]phenyl}sulphonyl)-piperidin-4-amine trihydrochloride Identical procedure to Example 35, but the dimethylamin hydrochloride is replaced by $NH_3$.
Melting point: 293-294° C.
Elemental Microanalysis:

|  | C | H | N | S | Cl |
|---|---|---|---|---|---|
| %, theory | 49.96 | 6.56 | 12.66 | 5.80 | 19.23 |
| %, experiment | 49.68 | 6.84 | 12.34 | 5.76 | 19.18 |

Pharmacological Study of Compounds of the Invention

Example A

Cerebral Levels of $N^t$-methylhistamine in the NMRI Mouse

The purpose of this study, which was carried out in accordance with the method of Taylor et al. (Biochem. Pharm., 1992, 44, 1261-1267), is to evaluate the ex vivo activity of the compounds of the present invention as antagonists of type $H_3$ central histamine receptors. That activity is revealed by measuring, after treatment intraperitoneally with the test compounds, the central levels of $N^t$-methylhistamine, which is a main metabolite of histamine. An increase in the cerebral concentrations of $N^t$-methylhistamine indicates an increase in the turn-over of histamine by blockage of the type $H_3$ central histamine receptors.

NMRI mice (18-20 g) are treated intraperitoneally or orally with compounds of the present invention or with their carrier (20 ml/kg). One hour after the pharmacological treatment, the animals are sacrificed, and their brains are removed, frozen in liquid nitrogen, weighed and homogenised in 0.1N $HClO_4$ at 4° C. The homogenised products are centrifuged (15 000 g, 17 min, 4° C.). The supernatants are recovered and divided into aliquots. The aliquots are frozen in, liquid nitrogen and stored at −80° C. until analysis.

Determination of the cerebral levels of N$^t$-methylhistamine is carried out by radioimmunological assay (RIA) using an assay kit. The tissue levels of N$^t$-methylhistamine are expressed in μg/g of fresh brain. The comparison of the cerebral levels of N$^t$-methylhistamine between animals treated with the carrier (controls) and animals treated with compounds of the present invention is carried out by single-factor variance analysis followed, if necessary, by a complementary analysis (Dunnett's test).

The results show that, at doses of from 1 to 10 mg/kg PO, the compounds of the present invention are capable of increasing endogenous cerebral concentrations of N$^t$-methylhistamine by 100%.

By way of example, the compounds of Examples 1, 5 and 9, administered at doses of 10 mg/kg PO, and the compound of Example 21, administered at a dose of 3 mg/kg PO, increase the endogenous cerebral concentrations of N$^t$-methylhistamine by 105%, 197%, 121% and 168%, respectively. These results demonstrate that the compounds of the present invention are powerful antagonists of type H$_3$ central histamine receptors.

Example B

Electroencephalographic Recordings on Freely Moving Rats

Adult male Wistar rats were chronically implanted with electrodes placed over the frontal and panetal cortex. Cortical electroencephalogram (EEG) was recorded from rats placed inside cages in a sound attenuating-room. Compounds and vehicle were administered in a random order at 10:00 AM on the same days with a minimum of 3 days between each administration, allowing each rat to serve as its own control. Absolute power of slow wave delta band activity (1-4 Hz), that predominates during slow wave sleep and disappears during wakefulness and rapid eyes movement sleep, was averaged over successive periods of 30 min. Over 30 min, low and high values of slow wave delta power are signs of arousal and sleep, respectively.

Results indicate that compounds of the present invention increase arousal (decrease of delta band activity) for doses ranging between 0.3 to 3 mg/kg IP.

By way of Example, the compound of Example 1, administered at a dose of 0.3 mg/kg, significantly reduce slow wave delta power during 150 minutes, a sign of cortical activation and arousal. At a dose of 3 mg/kg it is furthermore observed a significant delayed sleep latency: the first slow wave sleep episode occurs 73±5 minutes after the administration of compound of Example 1 whereas in the control group, this first slow wave sleep episode occurs at 45±5 minutes.

Example C

Pharmaceutical Composition

| Preparation formula for 1000 tablets each containing a dose of 100 mg of 4-({4-[6-(4-isopropylpiperazin-1-yl)pyridin-3-yl]phenyl}-sulphonyl)-morpholine dihydrochloride (Example 1) | 100 g |
|---|---|
| Hydroxypropylcellulose | 2 g |

-continued

| Wheat starch | 10 g |
|---|---|
| Lactose | 100 g |
| Magnesium stearate | 3 g |
| Talc | 3 g |

What is claimed is:
1. A compound selected from those of formula (I):

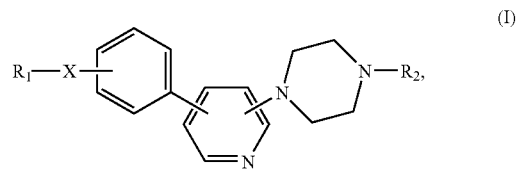

wherein:
X represents a C(O) or SO$_2$ group,
R$_1$ represents:
an aryl group,
or an NR$_3$R$_4$ group wherein R$_3$ and R$_4$, which may be the same or different, each independently represent a hydrogen atom, a linear or branched (C$_1$-C$_6$)alkyl group, a (C$_3$-C$_8$)cycloalkyl group or a (C$_3$-C$_8$)cycloalkyl-(C$_1$-C$_6$)alkyl group in which the alkyl moiety is linear or branched,
or R$_3$ and R$_4$, together with the nitrogen atom carrying them, form a 5- to 8-membered ring wherein one of the carbon atoms may be replaced by a nitrogen, oxygen or sulphur atom or by an SO or SO$_2$ group, wherein the ring thereby defined is optionally bridged by a linear or branched (C$_1$-C$_6$)alkylene group and is optionally substituted by one or more identical or different groups selected from halogen, linear or branched (C$_1$-C$_6$)alkyl, (C$_3$-C$_8$)cycloalkyl, linear or branched (C$_1$-C$_6$)alkoxy, linear or branched (C$_1$-C$_6$) polyhaloalkyl, carboxy, hydroxy, cyano, oxo, nitro and amino (optionally substituted by one or more linear or branched (C$_1$-C$_6$)alkyl groups),
R$_2$ represents a linear or branched (C$_1$-C$_6$)alkyl group, a (C$_3$-C$_8$)cycloalkyl group or a (C$_3$-C$_8$)cycloalkyl-(C$_1$-C$_6$)alkyl group wherein the alkyl moiety may be linear or branched,
it being understood that:
an aryl group means phenyl, naphthyl or biphenyl, wherein such groups may be optionally substituted by one or more identical or different groups selected from halogen, linear or branched (C$_1$-C$_6$)alkyl, linear or branched (C$_1$-C$_6$)alkoxy, linear or branched (C$_1$-C$_6$)polyhaloalkyl, carboxy, hydroxy, cyano, nitro and amino (optionally substituted by one or more linear or branched (C$_1$-C$_6$)alkyl groups),
its enantiomers and diastereoisomers, and addition salts thereof with a pharmaceutically acceptable acid or base.
2. A compound of claim 1, wherein R$_3$ and R$_4$, together with the nitrogen atom carrying them, form a 5- to 8-membered ring wherein one of the carbon atoms may be replaced by a nitrogen, oxygen or sulphur atom or by an SO or SO$_2$ group, wherein the ring thereby defined is optionally bridged by an alkylene chain, its enantiomers and diastereoisomers, and addition salts thereof with a pharmaceutically acceptable acid or base.
3. A compound of claim 1, wherein R$_1$ represents a morpholinyl, thiomorpholinyl, piperidyl, piperazinyl, 4-(alkyl)

piperazinyl, pyrrolidinyl, 2-(alkyl)-2,5-diazabicyclo[2.2.1]heptanyl or 2-oxa-5-azabicyclo[2.2.1]heptanyl group, its enantiomers and diastereoisomers, and addition salts thereof with a pharmaceutically acceptable acid or base.

4. A compound of claim 1, wherein X represents an $SO_2$ group, its enantiomers and diastereoisomers, and addition salts thereof with a pharmaceutically acceptable acid or base.

5. A compound of claim 1, wherein $R_2$ represents an isopropyl group, its enantiomers and diastereoisomers, and addition salts thereof with a pharmaceutically acceptable acid or base.

6. A compound of claim 1, which is 4-({4-[6-(4-isopropyl-piperazin-1-yl)pyridin-3-yl]phenyl}sulphonyl)morpholine dihydrochloride, and addition salts thereof with a pharmaceutically acceptable acid or base.

7. A process for the preparation of the compounds of formula (I) of claim 1, wherein a compound of formula (II):

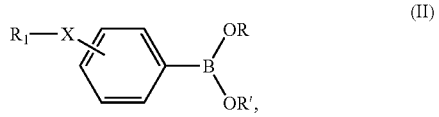

wherein R and R', which may be the same or different, each represent a hydrogen atom or a linear or branched ($C_1$-$C_6$)alkyl group or together form a linear or branched ($C_1$-$C_6$)alkylene chain, is condensed, in the presence of palladium(0), with a compound of formula (III):

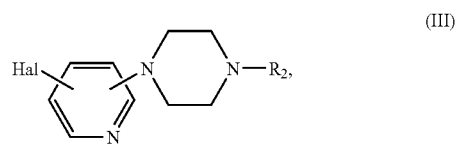

wherein Hal represents a halogen atom, to yield the compound of formula (I), which compound of formula (I) is purified, if necessary, according to a conventional purification technique, is separated, where appropriate, into its isomers according to a conventional separation technique and is converted, if desired, into its addition salts with a pharmaceutically acceptable acid or base.

8. A pharmaceutical composition comprising as active ingredient a compound of claim 1 in combination with one or more inert, non-toxic, pharmaceutically acceptable excipients or carriers.

9. A method for treating a living animal body, including a human, afflicted with a condition selected from convulsive attacks, attention deficit hyperactivity syndrome, obesity and narcoleptic states, comprising the step of administering to the living animal body, including a human, a compound of claim 1 which is effective for alleviation of the condition.

10. A method for treating a living animal body, including a human, afflicted with a condition selected form cognitive deficiencies associated with Alzheimer's disease comprising the step of administering to the living animal body, including a human, a compound of claim 1 which is effective for alleviation of the condition.

* * * * *